US009822489B2

(12) United States Patent
Stangler et al.

(10) Patent No.: US 9,822,489 B2
(45) Date of Patent: Nov. 21, 2017

(54) FLAVORED WIPE AND DISPENSING SYSTEM

(71) Applicant: TaylorBaby, LLC, Castle Rock, CO (US)

(72) Inventors: Danielle R. Stangler, Castle Rock, CO (US); Julia M. Rossi, Aurora, CO (US); Ryan Stangler, Castle Rock, CO (US)

(73) Assignee: TaylorBaby, LLC, Castle Rock, CO (US)

( * ) Notice: Subject to any disclaimer, the term of this patent is extended or adjusted under 35 U.S.C. 154(b) by 0 days.

(21) Appl. No.: 13/659,455

(22) Filed: Oct. 24, 2012

(65) Prior Publication Data

US 2013/0108722 A1 May 2, 2013

Related U.S. Application Data

(60) Provisional application No. 61/552,569, filed on Oct. 28, 2011.

(51) Int. Cl.
D21H 21/14 (2006.01)
D21H 27/00 (2006.01)

(52) U.S. Cl.
CPC ........... D21H 21/14 (2013.01); D21H 27/002 (2013.01)

(58) Field of Classification Search
None
See application file for complete search history.

(56) References Cited

U.S. PATENT DOCUMENTS

| | | | |
|---|---|---|---|
| 5,110,801 A | 5/1992 | Leveen et al. | |
| 5,320,772 A | 6/1994 | Tricca | |
| 6,361,784 B1 | 3/2002 | Brennan et al. | |
| 6,378,698 B1 | 4/2002 | Scoggins | |
| 6,486,104 B2 | 11/2002 | Patzer et al. | |
| 6,821,940 B2 | 11/2004 | Bullock et al. | |
| 7,201,271 B1 | 4/2007 | Saad | |
| 7,497,351 B2 | 3/2009 | Amundson et al. | |
| 7,674,058 B2 | 3/2010 | Sharp et al. | |
| 7,735,682 B1 | 6/2010 | Cassel et al. | |
| 7,943,165 B2 | 5/2011 | Doney et al. | |
| 8,632,636 B1 | 1/2014 | Tricca et al. | |
| 2002/0127937 A1 | 9/2002 | Lange et al. | |
| 2002/0164910 A1 | 11/2002 | Murray | |
| 2004/0031120 A1 | 2/2004 | Cherian | |
| 2004/0047905 A1* | 3/2004 | Padlo .................. | A61K 8/0208 424/465 |
| 2004/0071754 A1 | 4/2004 | Jupiter | |
| 2005/0074483 A1 | 4/2005 | Lange | |
| 2005/0079327 A1 | 4/2005 | Stiles | |
| 2006/0078515 A1 | 4/2006 | Kamrin-Balfour | |
| 2006/0151518 A1 | 7/2006 | Sarbo et al. | |
| 2006/0193898 A1 | 8/2006 | Norman | |
| 2007/0278242 A1 | 12/2007 | Amundson et al. | |
| 2007/0289988 A1 | 12/2007 | Sosalla et al. | |
| 2008/0038413 A1 | 2/2008 | Northrop | |
| 2008/0064278 A1 | 3/2008 | Oaroche | |
| 2008/0112902 A1* | 5/2008 | Perechocky ................. | 424/52 |
| 2008/0226803 A1* | 9/2008 | Letourneau et al. ......... | 426/597 |
| 2008/0311166 A1 | 12/2008 | Wimer | |
| 2009/0004355 A1 | 1/2009 | Catani | |
| 2009/0286437 A1 | 11/2009 | Cunningham et al. | |
| 2011/0206790 A1* | 8/2011 | Weiss ..................... | A01N 59/20 424/745 |
| 2012/0090113 A1 | 4/2012 | Manifold et al. | |
| 2013/0071887 A1 | 3/2013 | Wehrli | |
| 2014/0127152 A1 | 5/2014 | Goralczyk et al. | |
| 2014/0227421 A1 | 8/2014 | Markosyan | |
| 2015/0011493 A1 | 1/2015 | Laboureau et al. | |
| 2015/0050410 A1 | 2/2015 | Luo et al. | |
| 2015/0174015 A1 | 6/2015 | Stangler et al. | |

FOREIGN PATENT DOCUMENTS

| | | |
|---|---|---|
| CN | 103040688 | 4/2013 |
| JP | 08325156 | 12/1996 |
| JP | 2008-037758 | 2/2008 |
| JP | 2011-126795 | 6/2011 |
| WO | WO 98/17239 | 4/1998 |
| WO | WO 02/060419 | 8/2002 |
| WO | WO 2005/089782 | 9/2005 |
| WO | 2007-027269 A1 | 3/2007 |
| WO | WO 2007/094312 | 8/2007 |
| WO | WO 2008/134828 | 11/2008 |

(Continued)

OTHER PUBLICATIONS

International Search Report dated Mar. 18, 2013 for PCT/US2012/061673, 3 pp.
Official Action for Canadian Patent Application No. 2,888,009, dated Mar. 23, 2016, 4 pages.
Response to Official Action (dated Mar. 23, 2016) for Canadian Patent Application No. 2,888,009, dated Sep. 16, 2016; 10 pages.
Notice of Allowance for Canadian Patent Application No. 2,888,009, dated Nov. 9, 2016; 1 page.
Chart of Sweetners, 2014, 1 page.
"High Potency Sweetners," Sweet Green Fields, 2014, 1 page.
"Teeth Wipes by Confident White Smile: A Healthy Alternative for a Healthy Lifestyle," DMS Smile, Windsor, Ontario, Canada, 2014, retrieved from www.tcwipes.com, 2 pages.

(Continued)

Primary Examiner — Terry A McKelvey
Assistant Examiner — Catheryne Chen
(74) Attorney, Agent, or Firm — Sheridan Ross P.C.

(57) ABSTRACT

An example flavored wipe and method of manufacturing the flavored wipe includes a material configured for use as a wipe, and a solution comprising water and a flavoring component. The flavoring component may be stevia or other natural or artificial sweetener. An example dispensing system for the flavored wipe includes a compartment to hold a material configured for use as a wipe including a solution with at least a flavoring component. An opening is formed in the compartment to dispense the material and the solution from the compartment.

12 Claims, 7 Drawing Sheets

(56) References Cited

FOREIGN PATENT DOCUMENTS

| WO | WO 2009/071277 | 6/2009 |
|---|---|---|
| WO | 2010-017081 A2 | 2/2010 |
| WO | 2013-063102 A1 | 5/2013 |

OTHER PUBLICATIONS

Das et al., "Evaluation of safety and efficacy of Stevia Moisturiser Gel by Clinical Trial," Global J Medicinal Plant Res., 2013, vol. 1(2), pp. 228-233.
Written Opinion for International Patent Application No. PCT/US2012/061673, dated Mar. 18, 2013, 9 pages.

\* cited by examiner

FLAVORED WIPE AND DISPENSING SYSTEM

PRIORITY CLAIM

This application claims priority to, and the benefit of, U.S. Provisional Patent Application No. 61/552,569 filed Oct. 28, 2011 and titled "Wet Wipe" of Danielle R. Stangler and Ryan Stangler, which is hereby incorporated by reference in its entirety as though fully set forth herein.

BACKGROUND

Babies and toddlers inevitably get dirty faces. As a result, it is necessary to clean their faces frequently from time to time. However, babies and toddlers can also be fussy when it is time for their faces to be cleaned. Babies can practice several modes of "face wiping avoidance" and as a result, it can be a frustrating experience for a parent who is trying to clean his/her baby's face only to have the child turn away, scream, squirm, wiggle away, and generally resist having his/her face cleaned.

Moreover, children have very sensitive skin. This is particularly true of the facial area of the child. So, the frequent process of cleaning a child's facial area can result in irritation to the skin. This only adds to the further avoidance of the face wiping process by the child. If the skin gets irritated, it may become physically uncomfortable for the child to have their face wiped.

SUMMARY

There is currently the unsolved problem of how to clean a user's face effectively when the user (particularly a child) is being fussy. And there is also the problem of how to reduce or altogether eliminate irritating the user's skin. In accordance with an embodiment, a wet wipe is provided with flavoring. The flavoring can include a natural component, such as the natural flavoring known as stevia. (For purposes of this application, the word stevia is intended to have a broad meaning so as to encompass all types of stevia extracts, derivatives, solutions, or solids that are acceptable as additives for sweeteners or moisturizers unless specified with more particularity herein.) The stevia flavored wet wipe can provide a limited sweet taste for the wet wipe that does not create a negative impression on the child. Thus, when the parent goes to wipe the face of the child, the child does not resist being wiped with the wet wipe around the mouth area because the child knows that any trace solution imparted by the wet wipe will not taste bad—whether from direct contact with the wet wipe or from the residue left behind from the wet wipe solution on the child's face. Moreover, the wet wipe flavored with stevia will not leave behind a substantially sticky residue. Unlike sugar based products that do leave behind a sticky residue, stevia does not produce a sticky residue and therefore can serve as a useful cleaning additive as described herein.

In accordance with another embodiment, a wet wipe is provided with a moisturizer and/or soothing agent, such as the natural component known as stevia. The moisturizing and/or soothing properties of stevia allow the wet wipe to moisturize and/or soothe the skin of the child at the same time that the child is being cleaned with the wet wipe. So, not only is the child's face cleaned but it is moisturized and/or soothed at the same time. This has the opposite effect from most other wet wipes, because other wet wipes can actually irritate and/or damage a child's skin when the child's face is cleaned due to the materials of those wet wipes and solutions of the wet wipes. Yet another embodiment provides a wet wipe carrying a stevia solution that is formulated so as not to taste bad but also moisturizes the child's face. Further embodiments will also be apparent from the following disclosure.

DETAILED DESCRIPTION

As noted above, children can be very prone to getting their faces dirty while at the same time fussy when they need to have their faces cleaned. The child can get dirty from being fed, eating on their own, or playing in general. As a result, from time to time the child's face needs to be cleaned by a parent or caregiver. Some children resist being cleaned because they are generally fussy. Others have learned from experiences with other types of wet wipes that a bad taste or unpleasant sensation is encountered with those other types of wet wipes. For example, some wipes leave behind a bad tasting residue on the child's mouth area that tastes bad to the child. As a result, children are currently very resistant to having their faces cleaned in general and particularly cleaned by existing types of wet wipes.

In accordance with one embodiment of the invention, this notorious problem has finally been solved by providing the wet wipe with a natural flavoring known as stevia and sometimes referred to as stevia extract, as will be described in more detail below with reference to various example implementations. Briefly, however, a wet wipe may be configured to carry a stevia extract solution. The wipe may be used as an applicator to apply stevia extract to human skin. The pleasant taste of the stevia solution diminishes the fussiness by a user (e.g., a child or even an adult) when the user's face is wiped with the wipe. The wipe can also be used as a "sit still wipe," for example where the child licks the wipe while getting their diaper changed. The stevia extract solution can also be used to moisturize the user's skin.

In an example, a wet wipe is disclosed, including a material configured for use as a wipe; wherein the material carries a solution comprising water and a stevia extract. In another example, a method of cleaning the face of a child is disclosed, including wiping the face of the child with a wipe carrying a pre-determined solution comprising water and stevia extract. In another example, a method of moisturizing human skin is disclosed, including utilizing a wipe carrying a solution comprising a stevia extract to wipe the solution onto the skin. Still other examples will be apparent to those having ordinary skill in the art after becoming familiar with the teachings of the following disclosure.

Before continuing, it is noted that as used herein, the terms "includes" and "including" mean, but is not limited to, "includes" or "including" and "includes at least" or "including at least." The term "based on" means "based on" and "based at least in part on."

Figure 1:
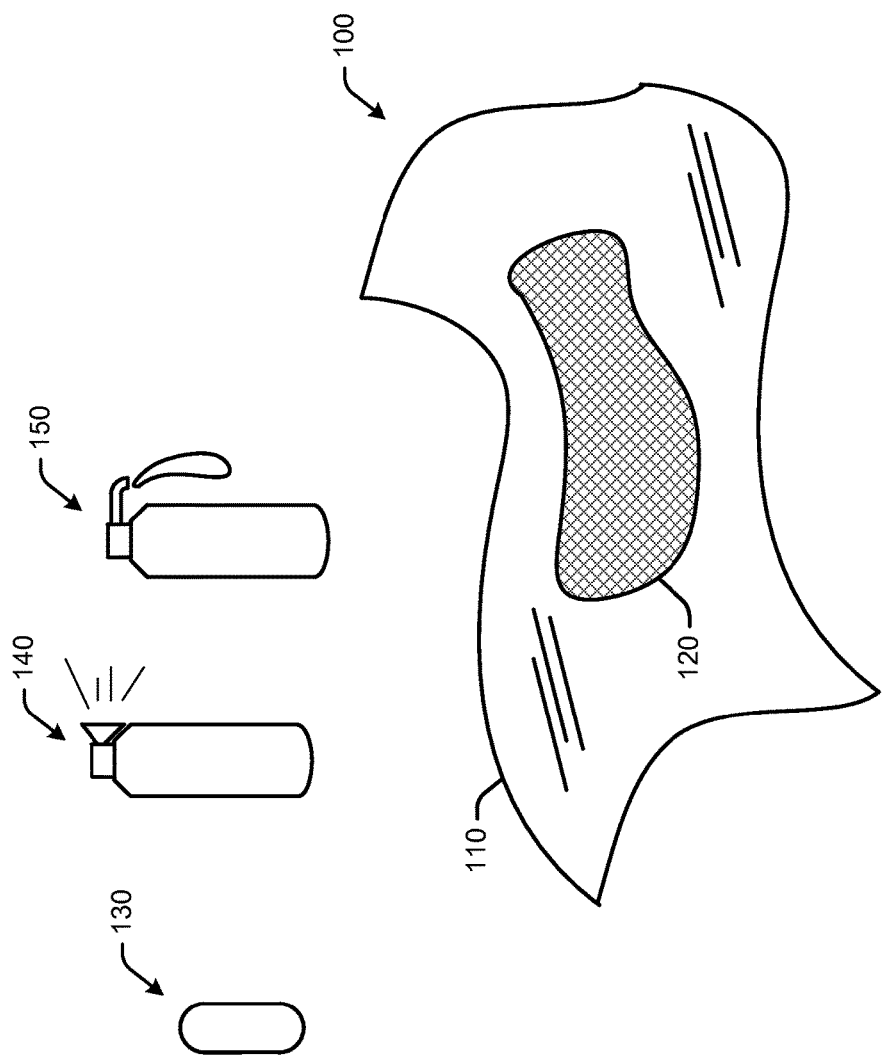
FIG. 1 is a perspective view of an example flavored wipe.

FIG. 1 is a perspective view of an example flavored wipe 100.

Figure 2:
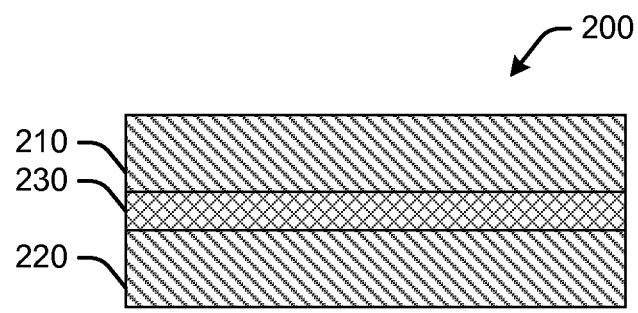
FIG. 2 is a cross-sectional view of an example flavored wipe such as the flavored wipe shown in FIG. 1.

FIG. 2 is a cross-sectional view of an example flavored wipe 200, such as the flavored wipe shown in FIG. 1. The flavored wipe 100 (or 200) may include a material 110 configured for use as a wipe, and a solution (illustrated in FIG. 1 by outline 120) comprising water and a flavoring component.

It is noted that the solution 120 may impregnate the entire wipe and/or only a portion of the wipe. For example, the solution may be provided on a corner of the wipe. Examples of the solution 120 will be described in more detail below. Briefly, however, the flavoring component may be a stevia extract.

The solution 120 may also include a cleaning agent, a moisturizing agent, a coloring agent, and/or a scenting agent. For example, the wipe 100 (or 200) may be a dual purpose (or multi-purpose) wipe, wherein a part of the wipe (e.g., a side or corner) includes a moisturizing agent and another part of the wipe (e.g., opposite side or corner) includes the flavoring component, and so forth. By way of illustration, half a single wipe 100 may be colored blue to indicate use as a hand cleaner (and thus include the cleaning agent) and the other half of the same wipe 100 may be colored green to indicate use as a flavored wipe (and thus include the flavoring component). Such an illustration may be desirable when the cleaner is for cleaning hands but should not be put in the mouth (e.g., the child's mouth, or even an adult's mouth such as for wiping teeth).

In an example, the material 110 is a dry compressed wipe and the solution (or at least the flavoring component) is added to the material from a vial (not shown) or a capsule 130. That is, the solution may be encapsulated and dissolved on the material (or separately dissolved and then applied to the material). In another example, the solution (or at least the flavoring component) is added to the material by spraying, for example with spray canister 140. The solution may also be evaporated from the material during manufacture, and the flavoring component is then activated prior to use by rehydration (e.g., by spraying water or other aqueous solution as illustrated by canister 140). In yet another example, the solution is emulsified and dispensed as a cream or lotion as illustrated by pump dispenser 150. The emulsified solution may also be dispensed from a squeezable tube having a small hole (or multiple holes in the cap), or provided in a "makeup" type compact for dipping the material into.

As illustrated in FIG. 2, the wipe may include a material such as a fiber-based textile 200 with fibers forming an outward raised/embossed texture on a first side 210 and/or second or opposite side 220. The fibers may be provided to remove/exfoliate skin during application of the solution on the skin. In an example, the solution may be provided in a separate layer 230. While three layers 210, 220, and 230 are shown in FIG. 2, it is noted that the material is not limited to any particular number of layers. Nor is the material not limited to having separate layers.

Also disclosed herein is a method of manufacturing a flavored wipe. In an example, the method may include providing a material (e.g., 110 in FIG. 1) configured for use as a wipe, and providing a solution (e.g., 120 in FIG. 1) for the material. The solution includes at least a flavoring component. As discussed above, the method may include providing the solution in dry form and activating the flavoring component immediately prior to use.

The stevia extract can be put into a solution that provides a sufficient amount of stevia extract per volume of water and with sufficient preservatives so as to resist degradation. For example, degradation can be resisted by making the wipe and/or solution resistant to microbial growth and/or pathogen growth. The amount of stevia extract added per volume of water (or volume of another non-harmful solution) should be sufficient to provide a sweet taste. For example, it should be sufficiently sweet that a majority (or a commercially significant minority) of children of a pre-determined age would rate the taste as "not bad" when surveyed. Alternatively, it could be manufactured with a sufficient sweetness that a majority (or commercially significant minority) of purchasing adults would rate the taste as "not bad." A taste that is rated as "not bad" is not necessarily "good" tasting. Rather, it is a taste that one would not try to avoid. Hence, the solution could be formulated to provide a taste that is not objectionable to a child—but not something that a child would try to ingest.

In accordance with one embodiment, the stevia solution can be prepared by combining stevia extract, such as Rebaudioside-A stevia, so that the stevia extract contributes 0.1 to 0.5% by weight of the final solution and the water accounts for the remaining percentage by weight.

Preservatives, such as potassium sorbate, sodium benzoate, and decyl glycoside can be added in appropriate amounts to prevent degradation of the stevia solution.

Other types of stevia and artificial or natural sweeteners could be used as well. For example, there are at least 240 different types of stevia. Some possible types for use in this product are believed to be Rebaudioside-A, Rebaudioside-C, Rebaudioside-D, and Stevioside.

In an example, the flavoring component may be a natural sweetener, selected from the group including but not limited to: Stevia, Luo han guo, Mogrosides, Monk Fruit, Monatin (from *Sclerochiton ilicifolius* plant), Cyclamate, and Brazzein.

In an example, the flavoring component may be an artificial sweetener, selected from the group including but not limited to: Sorbitol, Cyclamate, Saccharin, Aspartame, Sucralose, Acesulfame K, Acesulfame potassium, Neotame, Advantam, Isomtitol, mannitol, Lactitol, Isomalt, and lactitol.

In another embodiment, a solution can be mixed in the following contributions by weight percentage of the final product (e.g., 92.7% of the weight of the final product could be water). An example is illustrated in Table I.

TABLE I

Example Solution

| Component | Contribution (% by weight) |
| --- | --- |
| Water | 92.7-97.1 |
| Glycerin | 2.5-5.0 |
| Potassium Sorbate | 0.1-0.5 |
| Laurylglucosides Hydroxypropyl Sulfonate | 0.1-0.5 |

TABLE I-continued

Example Solution

| Component | Contribution (% by weight) |
|---|---|
| *Lonicera Caprifolium* (Honeysuckle) Flower Extract (and) *Lonicera Japonica* (Honeysuckle) Flower Extract | 0.1-.05 |
| Stevia | 0.1-0.5 |
| Citric Acid | 0.0-0.3 |

Of course, more or less water could be used for example, if some of these components are omitted or changed in amount.

The wet wipes can be prepared by utilizing nonwoven cloth suitable for absorbing solution. A roll of the cloth, preferably with pre-formed lengths of cloth suitable for use as wipes, can then be impregnated with the solution, for example. This is currently well-known by those of ordinary skill in the art. In accordance with one embodiment, the wipe material can be made from biodegradable material so that the wipe will degrade after being disposed of.

Another problem that is faced by parents who currently use wet wipes for children is that those wet wipes can irritate the child's skin—especially after repeated wiping of a child's face over time. This obviously damages the child's skin and makes it more sensitive to future wiping. Plus, it can reinforce the child's aversion to being wiped if the process is painful or irritating to the child.

In accordance with one embodiment, this problem has finally been solved by utilizing the natural moisturizer stevia to moisturize and/or soothe the child's skin at the same time that the child's skin is being cleaned. Thus, the wet wipe with a stevia extract moisturizer, for example, is able to both clean and moisturize the child's skin at the same time.

In accordance with the embodiment where moisturizing is desired, the amount of stevia extract added to the solution can be selected so as to provide a desired moisturizing capability. This may be the same amount or a different amount needed to achieve a desired taste from the solution. So, for example, where the product is intended for use solely as a moisturizing product, one might choose to add more stevia extract so as to produce a greater moisturizing effect on the skin. A similar approach could be followed to achieve a soothing function on the skin.

In accordance with another embodiment, additional additives can be added. For example, as noted above, preservatives may be added to protect the wipe/solution combination from degrading. One example of a preservative is honeysuckle extract. In addition, additives such as vitamin E, chamomile, aloe vera, polysorbate 80, annatto Extract, or natural oils might be added for the properties that those additives provide. For example, orange oil may be added for providing a scent, as well as an antibacterial function. In addition, sugarnat and/or polysorbate 80 can be used as a surfactant. Also, sodium benzoate can be used as a preservative. Green tea extract and aloe vera juice/extract may also be used.

In some embodiments, one might choose to use glycerin in addition to water. Glycerin can be used for its cleaning effect and non-toxic nature if consumed. Glycerin can also provide a moisturizing effect. However, glycerin is believed to have a disagreeable taste to children. So, it may be necessary to add more stevia than that required for water alone to mask the taste of the glycerin, should glycerin be used. It is noted that preservatives are the bad tasting parts of the formula. Glycerin also has a "soapy" taste. But stevia (or other sweeteners discussed herein) imparts a better taste.

In addition for use on a child's face, the wet wipes with moisturizing capability described herein can also be used on other parts of a child's skin. Moreover, they can be used by adults. Possible uses include, wipes for removing make-up; wipes for moisturizing adult skin; wipes for use during or after exercising; wiping the mouth of musical instruments; adding sweet flavor to the skin or other surfaces, wiping the faces of patients at hospitals, skilled nursing facilities, hospice care facilities, and nursing home facilities. Generally, the wipes may be used as non-durable consumer goods, cosmetic products, personal hygiene products, and baby products, for example.

In accordance with one embodiment, the wipe treated with stevia (or other sweetner) solution may be used as an applicator to human skin. For example, it might be used to apply the stevia extract to the face of an older person. Others have asserted that stevia can: help smooth out wrinkles; help heal skin blemishes and acne; help tighten skin like a facial mask; help hydrate skin (more than three times better than glycerin); can help enhance fragrances; can help provide anti-bacterial effect so as to improve shelf-life; help eliminate dandruff; can help treat seborrhea, dermatitis, and eczema. Thus, a wipe treated with stevia is a highly efficient way to apply stevia to the skin and particularly to the facial area that does not appear to have been appreciated by others.

In accordance with another embodiment, a wet wipe may be provided with antimicrobial and anti-pathogen properties by using stevia as part of the solution that is imparted on the wet wipe. Stevia has been asserted to exhibit antimicrobial and anti-pathogen properties. Thus, by using it as part of a solution for a wipe product, it is believed that a longer shelf life can be provided for the wipe product. Moreover, this can be accomplished through the use of a natural agent, such as stevia.

To prepare the wet wipes with the stevia solution, one may submerge a roll of wipe material within the stevia solution and allow it to soak for a sufficient time period to allow the solution to be imparted onto or impregnated within the wipe material. Alternatively, the solution may be sprayed or pumped onto the wipe material.

Thus, the use of stevia in a wipe product can address different problems. It can provide a taste that is not unpleasant, so that children will not avoid being wiped with the wipe. It is noted that sugar or other like sweeteners may leave a sticky residue behind. But the use of stevia (or other sweeteners disclosed herein) can provide the desired taste without leaving behind a sticky residue on a child's face. It can provide a soothing and/or moisturizing effect to human skin that counters the effects of a wipe irritating or damaging human skin. And, it can prolong shelf-life by exhibiting antimicrobial and/or anti-pathogen functions. Any of these functions independently or in various combinations can be useful in providing an improved wet wipe product.

Figure 3:
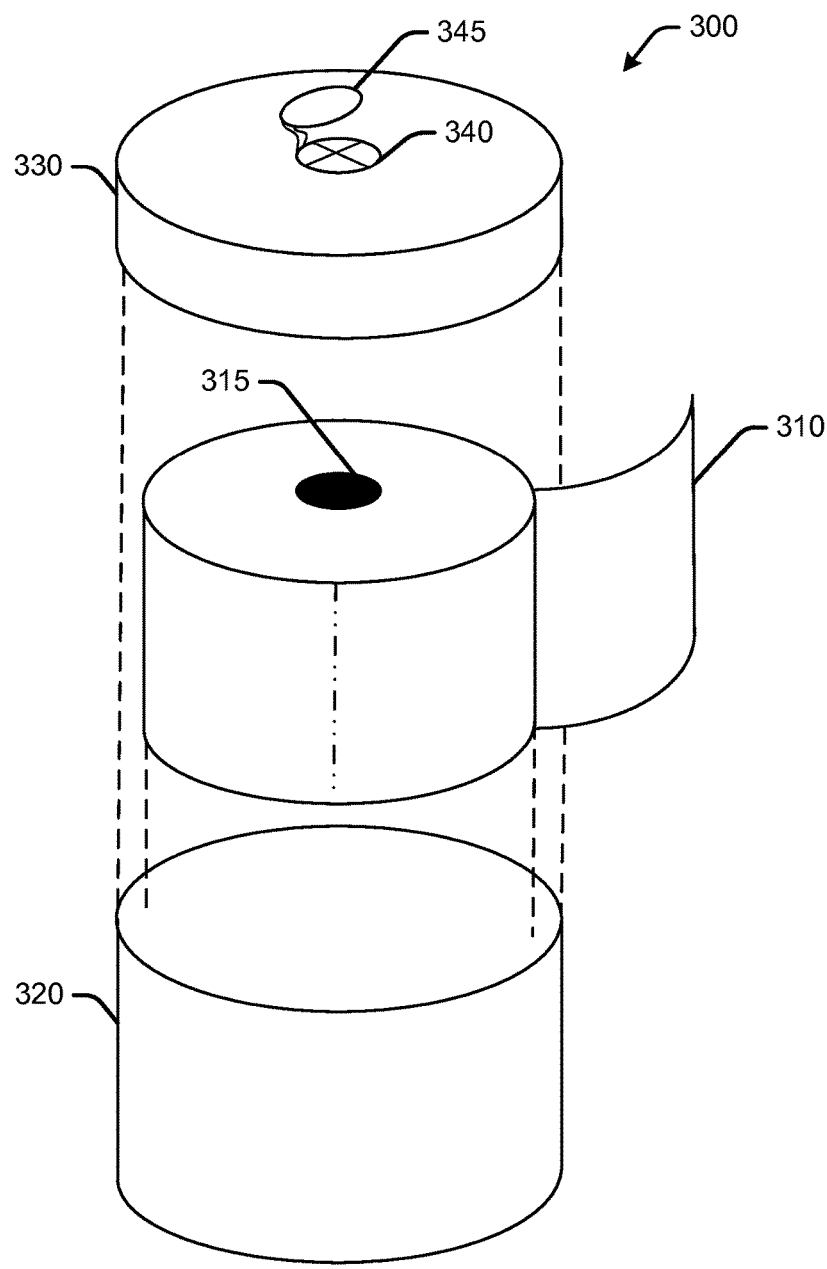
FIG. 3 is an exploded perspective view of an example dispensing system for a flavored wipe.

FIG. 3 is an exploded perspective view of an example dispensing system 300 for a flavored wipe 310. The dispensing system 300 may be any suitable shape and/or size. For example, the dispensing system 300 may be used as a diaper changing table canister. The dispensing system 300 may be fastened in any suitable manner, such as using hook-and-loop (VELCRO™) adhesive, sewn in place, clipped, etc. to a changing table or stroller, diaper bag, messenger bag, car seat, seat in a car, computer, tablet device, cell phone, purse, purse strap, fanny pack, belt loop, table, table in a restaurant, grocery cart, high chair, play gym, etc.

The dispensing system 300 may include a compartment 320 to hold a material configured for use as a wipe 310 including a solution with at least a flavoring component. The compartment 320 may be a hard container, or a soft-side pouch. In FIG. 3, the wipes 310 are shown as the wipes may be provided on a roll 315. The wipes 310 may be manually removed from the compartment 320 (e.g., by pulling) or automatically dispensed (e.g., using an electronic motor to turn the roll 315). The wipes 310 may be dispensed via a ticket-type dispenser (e.g., pull and tear), and even dispensed as part of a coin-operated system.

The wipes 310 are also shown on the roll 315 as the wipes 310 may be perforated for easy removal as the wipes 310 are pulled through the opening 340. However, the dispensing system 300 is not limited to use with wipes 310 on a roll 315. Other examples include, but are not limited to, precut and folded interlocking sheets, a napkin-type wipe (and "napkin" dispenser), or even a roll of individually packaged sachet pouches attached to each other by perforation.

The compartment may include a lid 330 with an opening 340 formed in the compartment to dispense the wipe 310 from the compartment 320. In an example, the opening may be slotted so as to reduce or altogether prevent evaporation of aqueous solution in the compartment 320. The opening may also be closed, e.g., as illustrated by closure flap 345.

In an example, the solution may be impregnated in the material prior to dispensing the wipes 310 from the compartment 320. In another example, the solution may be dried on the wipes 310 and activated by rehydrating the wipes 310 after dispending from the compartment 320. In yet another example, the solution may be added to dry wipes 310 (e.g., via the mechanisms illustrated in FIG. 1) after dispensing from the compartment 320.

Figure 4:
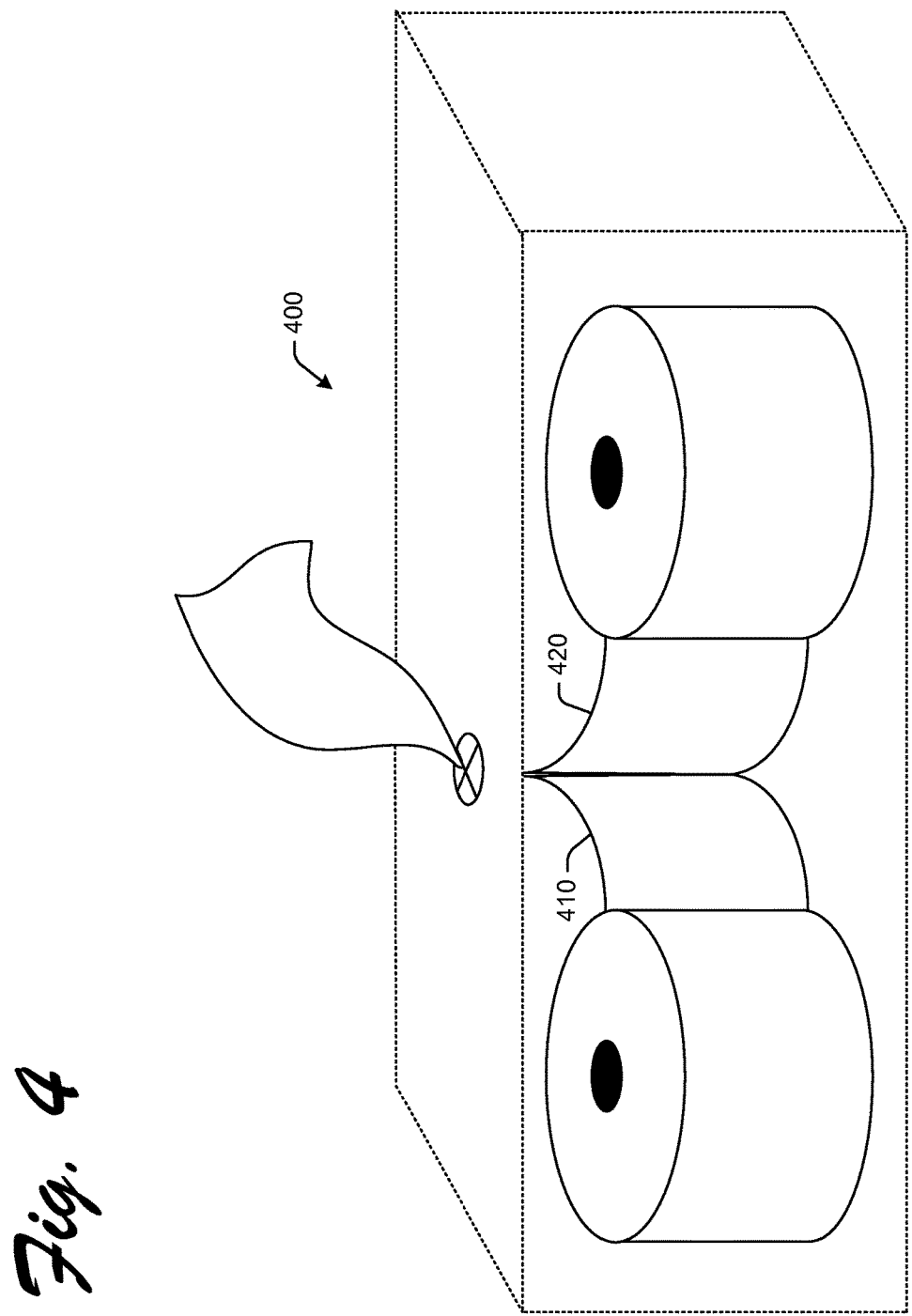
FIG. 4 is a phantom perspective view of another example dispensing system for a flavored wipe.

FIG. 4 is a phantom perspective view of another example dispensing system 400 for a flavored wipe 410. The dispensing system 400 in FIG. 4 is configured as a double sachet dispensing the material with the solution and simultaneously dispensing another material 420 with another agent (e.g., a cleaning agent), so that the two are provided on separate sheets to the user at the same time.

Figure 5:
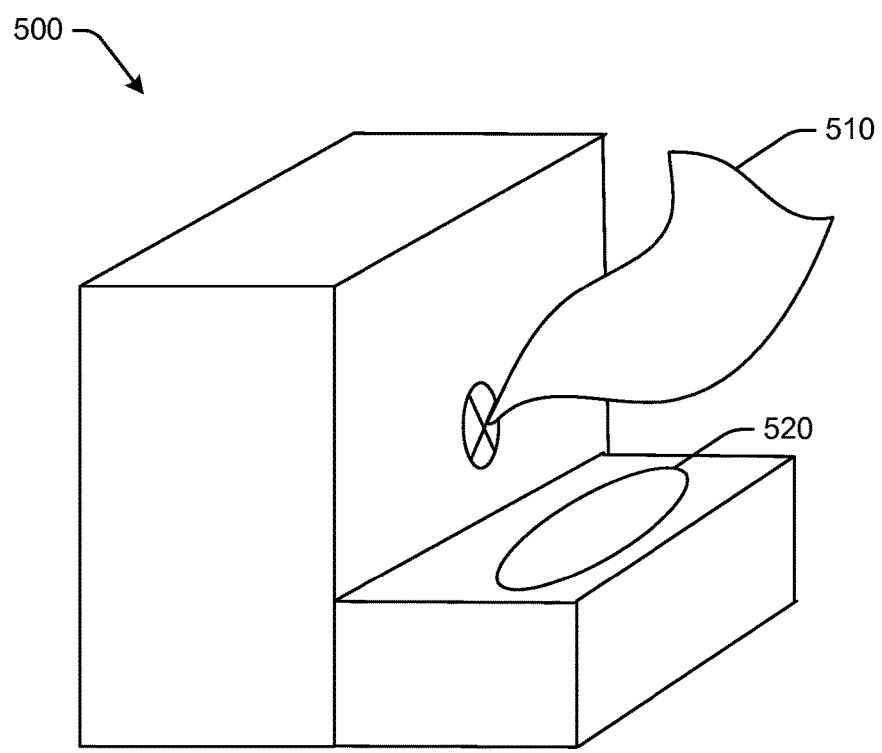
FIG. 5 is a perspective view of another example dispensing system for a flavored wipe.

FIG. 5 is a perspective view of another example dispensing system 500 for a flavored wipe 510. The dispensing system 500 in FIG. 5 is configured with another compartment 520 to contain the solution separate from the material. As such, the solution is impregnated in the material after dispensing the wipe 510 from the compartment.

Figure 6:
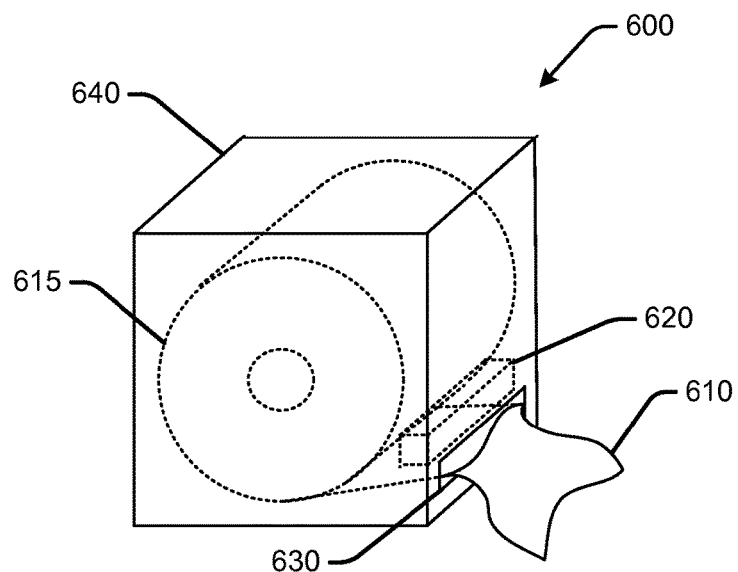
FIG. 6 is a perspective view of another example dispensing system showing the flavored wipes inside the dispensing system in phantom.
Figure 6A:
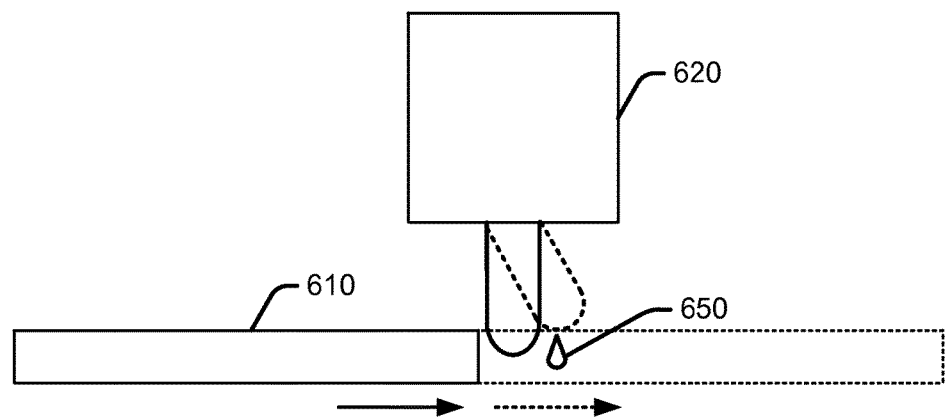
FIG. 6a is a detailed side view illustrating operation of an example applicator to apply a solution to the wipes as the wipes are dispensed from the dispensing system shown in FIG. 6.

FIG. 6 is a perspective view of another example dispensing system 600 showing the flavored wipes 610 on a roll 615 inside the dispensing system 600 in phantom. FIG. 6a is a detailed side view illustrating operation of an example applicator 620 to apply a solution (illustrated by drops 650) to the wipes 610 automatically as the wipes are dispensed from the dispensing system 600 shown in FIG. 6. In an example, the applicator 620 includes a valve (e.g., a silicon or other flexible valve) at the opening 630 of the compartment 640 which opens when moved as shown in FIG. 6 to apply solution 650 to the material as the wipe 610 travels (e.g., pulled) through the opening 630. Of course, the applicator 620 shown in FIG. 6 is illustrative and not limiting. Other manual and automatic applicators are also contemplated.

In an example, the dispensing system 600 may include a flexible plastic valve dispensing mechanism that allows only one wipe being pulled from a perforated roll within a canister. The wipe is pulled through the flexible valve. The valve creates friction and holds or "hugs" the wipe with just enough pressure to tear away one wipe at a time. The valve is soft and thus reduces or altogether prevents injury during use, such as may occur during use of metal or hard plastic wheels with teeth that grab the wipe as it is being pulled through the valve to rip the perforation. These "teethed" wheels may dispense more than one wipe, and the wipes can at times detach from the teeth so that the user has to dig it out of the canister through the valve with their finger(s). When this happens, the user is at a higher risk for hurting him or herself on the hard teeth. The user can also get their fingers stuck in the opening and when trying to pull their fingers out, the teeth can grip into the user's skin and cause pain or injury.

In an example, the valve disclosed herein may be recycled. Additionally, the valve functions more efficiently than wheels with teeth, allowing only one wipe out at a time, without the risk of the wipes falling back into the canister. Additionally, the valve is more effective because it creates a more air tight seal around the wipe as it is being "hugged" to prevent the wipes within the canister from drying out. The valve opening may be made no larger than the diameter of a quarter (25 cent piece).

Figure 7:
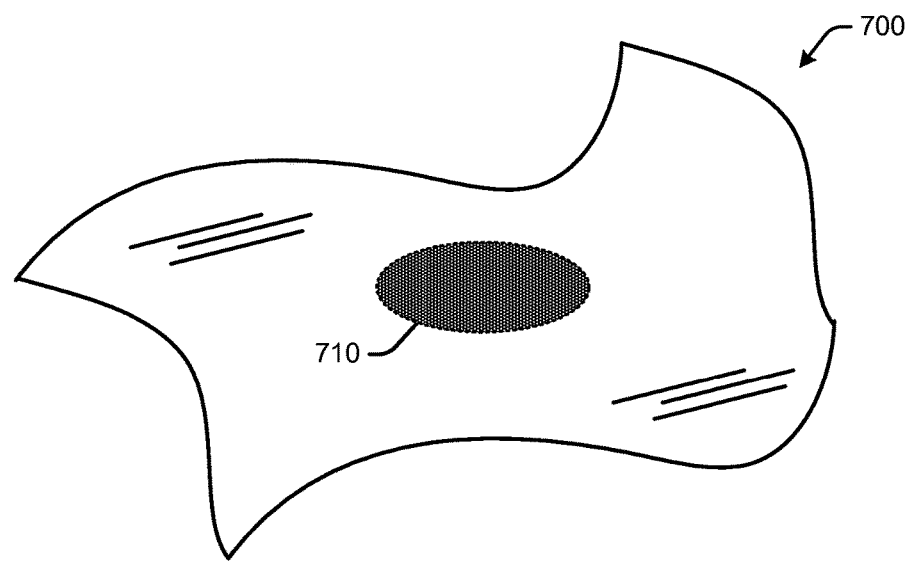
FIG. 7 is another example flavored wipe.
Figure 7A:
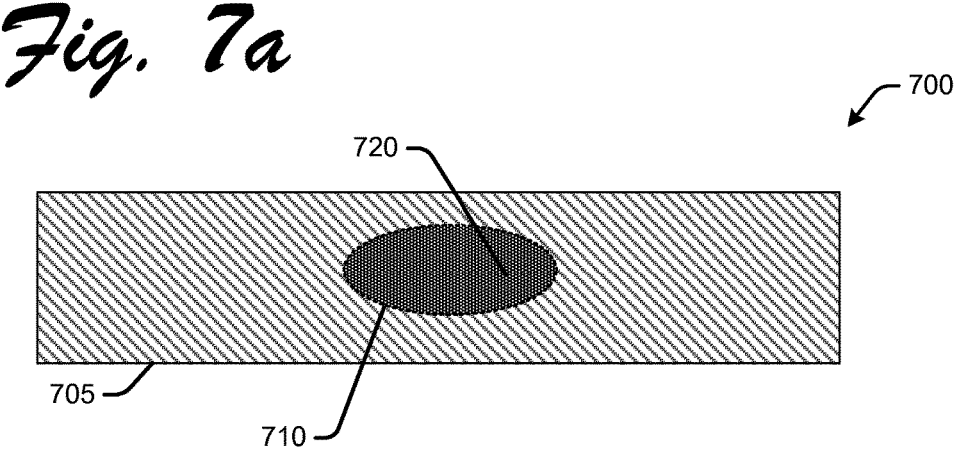
FIG. 7a is a cross-sectional view of the example flavored wipe shown in FIG. 7.

FIG. 7 is another example flavored wipe 700 showing a region 710 encapsulating the solution within the wipe 700 itself. FIG. 7a is a cross-sectional view of the example flavored wipe 700 shown in FIG. 7. In this example, the solution 720 is integral to the material 705 as a package, but not impregnated within the material. Instead, the solution is provided within region 710 in the material as a capsule (e.g., thin plastic pouch) that explodes onto the material as the wipe is dispensed (e.g., by being squeezed between rollers in the dispenser or crushed by the user's hands or other device).

It is also noted that many of the structures, materials, and acts recited herein can be recited as means for performing a function or step for performing a function. Therefore, it should be understood that such language is entitled to cover all such structures, materials, or acts disclosed within this specification and their equivalents, including any matter incorporated by reference.

It is thought that the apparatuses and methods of embodiments described herein will be understood from this specification. While the above description is a complete description of specific embodiments, the above description should not be taken as limiting the scope of the patent as defined by the claims.

It will be understood that while embodiments have been described in conjunction with specific examples, the foregoing description and examples are intended to illustrate, but not limit the scope of the invention. Other aspects, advantages, and modifications will be apparent to those of ordinary skill in the art to which the claims pertain. The elements and use of the above-described embodiments can be rearranged and combined in manners other than specifically described above, with any and all permutations within the scope of the disclosure.

The invention claimed is:

1. A flavored wipe, comprising:
    a material configured for use as a wipe; and
    a solution comprising water and a flavoring component including at least a sweetener comprising a stevia solution prepared by combining water and a stevia extract selected from the group consisting of Rebaudioside-A, Rebaudioside-C, Rebaudioside-D, and Stevioside, said stevia extract contributing from 0.1 to 0.5% b weight of the solution;
    wherein the stevia solution moisturizes a person's skin in the absence of another moisturizing agent.

2. The flavored wipe of claim 1, wherein the flavoring component comprises solely a sweetener comprising Rebaudioside-A.

3. The flavored wipe of claim 1, wherein said material has a texture to remove/exfoliate skin during application of the solution on the skin.

4. The flavored wipe of claim 1, wherein the stevia extract is Rebaudioside-A.

5. The flavored wipe of claim 1, wherein the wipe is resistant to microbial growth.

6. The flavored wipe of claim 1, wherein the wipe has anti-pathogen properties.

7. The flavored wipe of claim 1, wherein the stevia solution makes the wipe resistant to microbial growth.

8. The flavored wipe of claim 1, wherein the wipe is biodegradable.

9. The flavored wipe of claim 1, wherein the wipe is configured to reduce wrinkles, heal skin blemishes and acne, tighten skin, hydrate skin, enhance fragrance, reduce dandruff, treat seborrhea, treat dermatitis, and treat eczema.

10. The flavored wipe of claim 1, further comprising preservatives selected from the group consisting of potassium sorbate, sodium benzoate, and decyl glycoside.

11. The flavored wipe of claim 1, wherein said solution is 92.7% water by weight.

12. A flavored wipe, consisting essentially of:
a wipe material made from nonwoven cloth material;
said wipe material contacted with a solution comprising water and a flavoring A component, said flavoring component including at least a sweetener that does not mimic the taste of a natural fruit, comprising a stevia solution prepared by combining a stevia extract selected from the group consisting of Rebaudioside-A, Rebaudioside-C, Rebaudioside-D, and Stevioside, said stevia extract contributing from at least 0.1% by weight of the solution, wherein the stevia solution moisturizes a person's skin in the absence of another moisturizing agent.

* * * * *